United States Patent
Dive et al.

(10) Patent No.: US 6,482,797 B1
(45) Date of Patent: Nov. 19, 2002

(54) N-TERMINAL SITE SELECTIVE INHIBITORS OF HUMAN ANGIOTENSIN CONVERSION ENZYME (ACE)

(75) Inventors: Vincent Dive, Paloiseau (FR); Joël Cotton, Orsay (FR); Philippe Cuniasse, Paris (FR); Athanasios Yiotakis, Athens (GR); Pierre Corvol, Paris (FR); Annie Michaud, Nontrfuil (FR); Marie-Thérèse Chauvet, Seures (FR); Joël Menard, Paris (FR); Eric Ezan, Matekoff (FR)

(73) Assignees: Commissariat A l'Energie Atomique, Paris (FR); Institut National de la Sante et de la Recherche Medicale Inserm, Paris (FR)

( * ) Notice: Subject to any disclaimer, the term of this patent is extended or adjusted under 35 U.S.C. 154(b) by 0 days.

(21) Appl. No.: 09/719,573

(22) PCT Filed: Jul. 1, 1999

(86) PCT No.: PCT/FR99/01581
§ 371 (c)(1),
(2), (4) Date: Jan. 30, 2001

(87) PCT Pub. No.: WO00/01706
PCT Pub. Date: Jan. 13, 2000

(30) Foreign Application Priority Data

Jul. 2, 1998 (FR) .............................. 98 08464

(51) Int. Cl.$^7$ ......................... A61K 38/00; A61K 38/16; C07K 5/00
(52) U.S. Cl. .............................. 514/2; 514/7; 530/300; 530/330; 530/340
(58) Field of Search ................................ 530/300, 340, 530/330; 514/7, 2

(56) References Cited

FOREIGN PATENT DOCUMENTS

| EP | 0 209 848 | 1/1987 | |
|---|---|---|---|
| EP | 0 725 075 | 8/1996 | |
| EP | 0725075 | * 8/1996 | ............ C07K/5/03 |
| FR | 2 676 059 | 11/1992 | |
| WO | WO 98/18803 | 5/1998 | |

OTHER PUBLICATIONS

Jiracek et al. (Development of the First Potent and Selective Inhibitor of the Zinc Endopeptidase Neurolysin Using a Systematic Approach Based on combinational Chemistry of Phosphinic Peptides, J. Biol. Chem., vol. 271, (9), 1996, 19606–19611).*

Jiracek et al.(Development of high Potent and Selective Phosphonic Peptide Inhibitors of Zinc Endopeptidase 24–15 Using Combinatorial Chemistry, J. Biol. Chem., vol. 270, (15), 1995, 21701–21706).*

F. Soubrier, et al., Proc. Natl. Acad. Sci. USA, vol. 85, pp. 9386–9390, "Two Putative Active Centers in Human Angiotensin I–Converting Enzyme Revealed By Molecular Cloning", Dec. 1988.

M. Lenfant, et al., Proc. Natl. Acad. Sci. USA, vol. 86, pp. 779–782, "Inhibitor of Hematopoietic Pluripotent Stem Cell Proliferation: Purification and Determination of Its Structure", Feb. 1989.

M.–N. Lombard, et al, Cell Tissue Kinet., pp. 99–103, "In Vivo Effect of the Tetrapeptide, N–Acetyl–SER–ASP–LYS–PRO, on the $G_1$–S Transition of Rat Hepatocytes", 1990.

A.E. Bogden, et al., Annals New York Academy of Science, pp. 126–139, Amelioration of Chemotherapy–Induced Toxicity By Cotreatment with AcSDKP, A Tetrapeptide Inhibitor of Hematopoietic Stem Cell Proliferation.

A. Rousseau, et al., The journal of Biological Chemistry, vol. 270, No. 8, pp. 3656–3661, "The Hemoregulatory Peptide N–Acetyl–SER–ASP–LYS–PRO is a Natural and Specific Substrate of the N–Terminal Active Site of Human Angiotensin–Converting Enzyme", 1995.

M. Azizi, et al., Rapid Publication, vol. 97, No. 3, pp. 839–844, "Acute Angiotensin–Converting Enzyme Inhibition Increases the Plasma Level of the Natural Stem Cell Regulator N–Acetyl–Seryl–Aspartyl–Lysyl–Proline", Feb. 1996.

O. V. Volpert, et al., Captopril and Angiogenesis, vol. 98, No. 3, pp. 671–679, "Captopril Inhibits Angiogenesis and Slows the Growth of Experimental Tumors in Rats", Aug. 1996.

A. Yiotakis, et al., The Journal of Organic Chemistry, vol. 61, No. 19, pp. 6601–6605, "Protection of the Hydroxyphosphinyl Function of Phosphinic Dipeptides By Adamantyl. Application to the Solid–Phase Synthesis of Phosphinic Peptides", 1996.

K. Barlos, et al., Int. J. Peptide Protein Res., vol. 37, pp. 513–520, "2–Chlorotrityl Chloride Resin", 1991.

(List continued on next page.)

Primary Examiner—Jeffrey Fredman
(74) Attorney, Agent, or Firm—Oblon, Spivak, McClelland, Maier & Neustadt, P.C.

(57) ABSTRACT

The invention relates to peptide derivatives that can be used as selective inhibitors of the N-terminal site of human angiotensin-converting enzyme.

The derivatives comprise the amino acid sequence with the following formula:

-Asp-Phe-Ψ(PO$_2$CH$_2$)-Ala-Xaa'-    (I)

wherein:
Ψ(PO$_2$CH$_2$) indicates that the peptide bond (CONH) between Phe and Ala has been replaced by the phosphonic bond PO$_2$CH$_2$, and
Xaa' represents an amino acid residue.

They can be used in pharmaceutical formulations, particularly to protect haematopoietic strain cells of patients undergoing aggressive chemotherapy or radiotherapy treatment.

31 Claims, 6 Drawing Sheets

OTHER PUBLICATIONS

Jiří Jiráček, et al., The Journal of Biological Chemistry, vol. 270, No. 37, pp. 21701–21706, "Development of Highly Potent and Selective Phosphinic Peptide Ihibitors of Zinc Endopeptidase 24–15 Using Combinatorial Chemistry", Sep. 15, 1995.

Jiří Jiráček, et al., The Journal of Biological Chemistry, vol. 271, No. 32, pp. 19606–19611, "Development of the First Potent and Selective Inhibitor of the Zinc Endopeptidase Neurolysin Using a Systematic Approach Based on Combinatorial Chemistry of Phosphinic Peptides", Aug. 9, 1996.

Lei Wei, et al., The Journal of Biological Chemistry, vol. 267, No. 19, pp. 13398–13405, "The Two Homologous Domains of Human Angiotensin I–Converting Enzyme Intract Defferently with Competitive Inhibitors", Jul. 5, 1992.

E.K. Baylis, et al., J. Chem. Soc. Perkin. Trans., pp. 2845–2853, "1–Aminoalkylphosphonous Acids. Part 1. Isosteres O The Protein Amino Acids". 1984.

* cited by examiner

CAPTOPRIL

ENALAPRIL

FOSINOPRIL

N-TERMINAL SITE SELECTIVE INHIBITORS OF HUMAN ANGIOTENSIN CONVERSION ENZYME (ACE)

FIELD OF THE INVENTION

The present invention relates to a phosphinic peptide derivative, capable of selectively inhibiting the N-terminal site of human angiotension conversion enzyme (ACE) without the second active site of ACE.

Said peptide derivatives which are selective inhibitors of the N-terminal site of ACE may be used for therapeutic purposes to protest haematopoietic strain cells of patients undergoing aggressive chemotherapy or radiotherapy.

STATE OF THE RELATED ART

In the 1980s, the development of pseudo-peptide ACE inhibitors genuinely revolutionised the treatment of arterial hypertension, heart failure and chronic kidney failure. In this way, there is now a wide range of synthetic ACE inhibitors which are used in clinical practice. Of these, captopril, enalapril and fosinopril, the formulas of which are given in FIG. 1, are known.

In parallel with this work, due to the cloning of ACE enzyme in 1988, P. Corvol's group was able to demonstrate the existence of two active sites in said enzyme, as described by Soubrier et al. in Proc. Natl. Acad. Sci. USA (1988) 85, 9386–9390 [1].

The formal demonstration that said two active ACE site control separate physiological functions in humans, represents another revolution in this field and has significant consequences in therapeutic terms. Given that all the ACE inhibitors developed to date inhibit in vitro both active ACE sites to a similar degree, the physiological function of said two active sites in vivo cannot be treated with this type of compound. However, the first inhibitors capable of discriminating between the two active ACE sites would be extremely valuable.

ACE hydrolyses several natural substrates involved in regulating arterial pressure, the circulating blood volume and cardiovascular haemodynamics. The main substrate is angiotensin I, an inactive decapeptide, which is activated to angiotension II, a vasopressor and antinatriuretic peptide, after hydrolysis of the His-Leu carboxyterminal dipeptide. In parallel, ACE inactivates bradykinin, a vasodilator and natriuretic peptide, into a heptapeptide and then into a pentapeptide, both inactive. The two N- and C-terminal sites of ACE are involved in this hydrolysis in a similar fashion.

A specific function of the N-terminal of ACE was recently identified by P. Corvol's group. As described by Lenfant et al. in Proc. Natl. Acad. Sci. USA (1989), 86, 779–782 [2], the N-Acetyl-Seryl-Aspartyl-Lysyl-Proline (AcSDKP) is a natural circulating inhibitor of the entry into S phase of haematopoietic strain cells. It also inhibits the entry into S phase of other cell types such as hepatocytes in regeneration phase, lymphocytes and several stable cell lines, as described by Lombard et al, in Cell. Tissue. Kinet (1990) 23, 99–103 [3]. The inhibitory action of AcSDKP on the cell cycle of haematopoietic cells is specific to normal haematopoietic cells; leucaemic cells are not concerned. Therefore, AcSDKp was proposed as a therapeutic agent for the protection of medullary progenitors during chemotherapy. In fact, administering AcSDKP prolongs the survival of mice treated with cytotoxic agents (Bodgen et al, Ann. N.Y. Acad. Sci. (1991) 628, 126–139 [4]). As described by Rousseau et al in J. Biol. Chem. (1995) 270, 3656–3661 [5] and Azizi et al in J. Clin. Invest. (1996) 97, 839–844 [6], AcSDKP is hydrolysed in vitro and in vivo by ACE, and more particularly by the N-terminal domain of the enzyme. In vitro, AcSDKP is hydrolysed 50 times more quickly by the N-terminal domain than by the C-terminal domain. This discovery demonstrates that it would be possible to develop specific inhibitors of the N- or C-terminal domain of ACE, making it possible to act on substrates involved in functions other than arterial pressure regulation and the hydrosodium metabolism.

ACE is the main, or even exclusive enzyme in the metabolism of plasma AcSDKP. Administering a single dose of captopril in healthy volunteer subjects increases the plasma level of the peptide 6 to 7-fold. A selective inhibitor of the N-terminal domain would make it possible to obtain such a result without modifying, unlike captopril and the other converting enzyme inhibitors used to date, the metabolism of the peptides playing a role in the control of arterial pressure and the hydrosodium metabolism (angiotensin, bradykinin). Therefore, ACE N-terminal domain inhibitors would be of great interest for the protection of haematopoietic strain cells of patients undergoing aggressive chemotherapy or radiotherapy treatment. The inhibitor could be administered before or concomitantly with the anti-cancer treatment.

In addition, it was recently demonstrated, by Volpert et al in J. Clin. Invest. (1996) 98, 671–679 [7] that captopril, which inhibits both active sites of ACE, could experimentally exert a protective, anti-cancer, effect in vitro and in vivo. The mechanism of this protective effect is not known but most probably involves AcSDKP, due to its properties on the entry in the cell cycle of numerous types of cells. Therefore, a selective inhibitor of the N-terminal domain of ACE, potentialising the plasma level of AcSDKP, without modifying the metabolism of vasoactive peptides, could have a beneficial effect.

Most of the strong ACE inhibitors developed to date and illustrated in FIG. 1 are characterised by the presence of a pseudo-dipeptide cell on which a chemical group capable of interacting favourably with the zinc atom located in the active ACE site has been grafted. Indeed, ACE belongs to the zinc metalloprotease group and is characterised by the presence of a zinc atom in both active sites of the enzyme, the zinc atom playing an essential role in catalysis. Numerous studies have demonstrated that the synthesis of pseudo-peptides comprising chemical groups capable of chelating zinc offered access to very powerful zinc metalloprotease inhibitors. The chemical groups capable of interacting with zinc include in the commercial ACE inhibitors, the HS thiol group (captopril), the CH—COO carboxyalkyl group (enalapril) and the $PO_2$—X phosphoryl group where X=NH, O,$CH_2$ (Fosinopril).

The documents FR-A-2 676 059 [8] and EP-A-0 725 075 [9] illustrate peptide derivatives that can be used as zinc protease inhibitors, which comprise phosphinic type groups to interact with zinc. In FR-A-2 676 059, said derivatives are bacterial collagenase inhibitors while in EP-A-0 725 075, they are selective 24-15 zinc endopeptidase inhibitors, which are inactive with respect to other proteases such an angiotensin-converting enzyme.

In this way, to date, there were no selective inhibitors of the N-terminal site of angiotensin-converting enzyme. The present invention specifically relates to new peptide derivatives comprising a phosphinic group, which are selective inhibitors of the N-terminal site of said enzyme.

DESCRIPTION OF THE INVENTION

According to the invention, said new peptide derivatives comprise the amino acid sequence according to the following formula:

-Asp-Phe-Ψ(PO$_2$CH$_2$)-Ala-Xaa'-   I wherein:

Ψ(PO$_2$CH$_2$) indicates that the peptide bond (CONH) between Phe and Ala has been replaced by the phosphinic bond PO$_2$CH$_2$, and Xaa' represents an amino acid residue. In this sequence, the PO$_2$CH$_2$ group is in PO$_2^-$ form; therefore, it is associated with a counter-ion such as K$^+$, Na$^+$ or any other pharmacologically acceptable metal. The type of counter-ion is of no significance since, in water, charged groups are dissociated.

According to a particular embodiment of the invention, the peptide derivative comprises only the four amino acids of this sequence and observes the following formula:

R$^1$-Asp-Phe-Ψ(PO$_2$CH$_2$)-Ala-Xaa'-NH$_2$   II wherein:

R$^1$ represents the acetyl or benzyloxycarbonyl group,

Ψ(PO$_2$CH$_2$) indicates that the peptide bond (CONH) between Phe and Ala has been replaced by the phosphinic bond PO$_2$CH$_2$, and Xaa' represents an amino acid residue.

Preferentially, R$^1$ represents the acetyl group.

In formulas I and II given above, the amino acids used for Xaa' may be natural or non-natural amino acids, or pseudo-amino acids.

The natural amino acids may be selected from alanine, arginine, asparagine, aspartic acid, cysteine, glutamine, glutamic acid, glycine, histidine, isoleucine, leucine, norleucine, lysine, methionine, phenylalanine, proline, hydroxyproline, serine, threonine, tryptophan, tyrosine, valine, nitrophenylalanine, homoarginine, thiazolidine and dehydropoline.

A pseudo-amino acid may be defined as an amino acid wherein the amino or carbonyl function has been replaced by another chemical group.

In said formulas, the amino acids Asp, Phe, Ala and Xaa' may be in L or D form. Therefore, the peptide derivative may be composed of a single isomer or of a mixture of 4 diastereoisomers, due to the presence of two asymmetric centres in the derivative.

In the peptide derivative according to the invention, the amino acid Xaa' is preferentially selected from the following amino acids: Pro, Ala, Thr, Lys and Leu which has a low activity with respect to the C-terminal site of ACE.

Preferentially, Xaa' represents Ala since this amino acid reinforces the activity of the peptide derivative for the inhibition of-the N-terminal site of the enzyme while having a low inhibitory activity on the C-terminal site.

The peptide derivatives according to the invention are different from the peptide derivatives described in EP-A-0 725 075 in that they comprise before the pseudo-Phe an Asp residue which makes it possible to render the peptide derivative inactive with respect to the C-terminal site of angiotensin-converting enzyme and thus provide the required selectivity. In addition, the peptide derivatives according to EP-A-0 725 075 were inactive with respect to this enzyme while the derivatives according to the invention are active with respect to the N-terminal part of said enzyme.

The presence of Asp and pseudo-Phe residues enables the peptide derivatives to act on sub-sites S1 and S2 of the enzyme, which is an unusual property for an ACE inhibitor. An even more surprising fact is that said peptide derivative comprises a carboxylate group in the C-terminal position of its structure, while all the ACE inhibitors described to date have systematically comprised a free carboxamide group. In this way, said peptide derivative appears to be very original bother in terms of its chemical structure and its inhibiting activity.

According to the invention, although any Phe and Ala amino acid configuration may be suitable, it is preferable for Phe to have the R configuration. In addition, it is also preferable for the Ala amino acid residue to have the S configuration. In this way, the preferred peptide derivative observes the formula:

Ac-Asp-$_{(R)}$Phe-Ψ(PO$_2$CH$_2$)-$_{(S)}$Ala-Ala-NH$_2$   III wherein:

Ac represents the acetyl group, and

Ψ(PO$_2$CH$_2$) indicates that the peptide bond (CONH) between Phe and Ala has been replaced by the phosphinic bond (PO$_2$CH$_2$).

The peptide derivatives according to the invention may be prepared using conventional processes such as that described in FR-A-2 676 059 or using a solid phase synthesis process such as that described in EP-A-0 725 075 on the basis of the synthon of the formula:

Fmoc-PheΨ(PO(Ad)-CH$_2$)AlaOH where Fmoc represents the (fluorenylmethoxyl)carbonyl group and Ad represents the adamantyl group, and using 2-chloritrityl resin as a solid substrate.

This synthon may be prepared in particular according to the protocol described by Yiotakis et al in J. Org. Chem., 1996, 61, 6601–6605[10].

The invention also relates to a pharmaceutical formulation selectively inhibiting the N-terminal site of human angiotensin-converting enzyme, which comprises a peptide derivative according to formula I, II or III given above.

Said pharmaceutical formulation can particularly be used to protect haematopoietic strain cells of patients undergoing aggressive chemotherapy or radiotherapy treatment, for example cancer treatment.

The invention also relates to the use of a peptide derivative according to formula I, II or III described above to produce a medicinal product selectively inhibiting the N-terminal site of human angiotensin-converting enzyme.

Such a medicinal product may be intended to regulate the proliferation of haematopoietic strain cells of patients undergoing cancer treatment.

The invention's other characteristics and advantages will be seen more clearly upon reading the following description, which is naturally given as an illustration and is not restrictive, with reference to the appended figures.

DETAILED DESCRIPTION OF EMBODIMENTS

EXAMPLE 1

Figure 1:
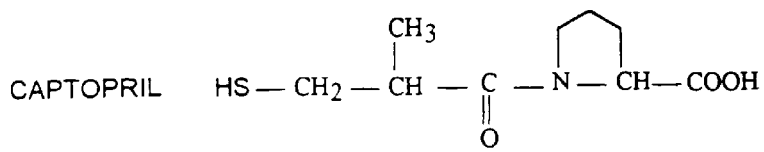
FIG. 1 already described illustrates the structure of known human angiotensin-converting enzyme, according to the prior art.
Figure 1:
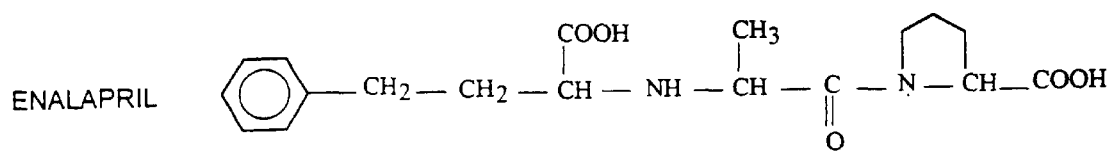
Figure 1:
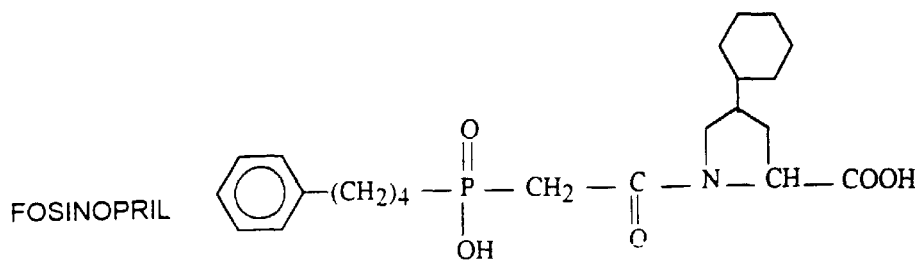

In this example, twenty mixtures according to the general formula Ac-Xaa-PheΨ(PO$_2$CH$_2$)Ala-Xaa'-NH$_2$ were synthesised, wherein the Xaa position is occupied by an amino acid of known structure, while in the Xaa' position, the twenty natural amino acids are represented in an equimolecular fashion.

For this synthesis a combinatory chemical approach described by Jiracek et al in J. Biol. Chem. (1995) 270, 21701–21706, [12] and Jiracek et al, J. Biol. Chem. (1996) 271, 19606–16661, [13] was used along with a solid phase synthesis using, as the phosphinic block, the synthon Fmoc-PheΨ(PO(Ad)—CH$_2$)AlaOH, obtained according to the procedure described by Yiotakis et al in J. Org. Chem. (1996) 61, 6601–6605, [10] for type 5 synthons.

a) Fmoc-PheΨ(PO(Ad)—CH$_2$)AlaOH phosphinic block synthesis.

1. Preparation of Z-Phe(PO$_2$—CH$_2$)AlaOet block (Z=benzyloxycarbonyl).

A suspension of Z-Phe(PO$_2$)H (1 mmol) and hexamethyldisilazane (5 mmol) is heated to 110° C., in an argon atmosphere for 1 hour. After cooling to 90° C., ethyl methylacrylate (1.3 mmol) is added dropwise for 30 minutes. The reaction is left to stand for 3 hours, with stirring, at 90° C. After bringing the reaction mixture to a temperature of 70° C., 3 ml of absolute ethanol are added dropwise. After returning to ambient temperature, the volatile products are eliminated by evaporation in a vacuum, and the remaining product is taken up in 10% NaHCO$_3$. This aqueous phase is rinsed with ether, acidified to pH 1.5 with 1N HCl, and the precipitate is then taken up in ethyl acetate. The organic phase is dried with Na$_2$SO$_4$, evaporated to dryness to produce the Z-Phe(PO$_2$—CH$_2$)AlaOet block with a good yield.

2) Preparation of the Z-Phe(PO(Ad)—CH$_2$)AlaOet block.

The Z-Phe(PO$_2$—CH$_2$)AlaOet compound (1 mmol) is dissolved in 95% ethanol (25 ml). This solution is added dropwise to a 0.5 M silver nitrate solution. After 10 minutes, 15 ml of water are added to the reaction mixture and the ethanol is evaporated in a vacuum. The remaining aqueous phase, containing the silver precipitate, is cooled with a water and ice bath. The precipitate formed is filtered, washed with cold water, and dried in a vacuum in the presence of P$_2$O$_5$, to produce a silver salt of the phosphinic block with a 90% yield. This product (1 mmol) is added to an adamantyl bromide solution (1.2 mmol) in chloroform (10 ml). This mixture is reflux boiled for 30 minutes. The silver bromide, which precipitates, is eliminated by filtration, and the remaining reaction mixture is evaporated to dryness in a vacuum. The expected product is purified by flash chromatography (eluent: chloroform/isopropanol, 9:3) with an 80% yield.

3) Preparation of the Z-Phe(PO(Ad)—CH$_2$)AlaOH block.

The Z-Phe(PO(Ad)—CH$_2$)AlaOH block (1 mmol) is dissolved in ethanol (10 ml). 1 ml of 4N soda is added to this solution, dropwise. After 2 hours of reaction, the ethanol is evaporated in a vacuum, and the residue diluted in 20 ml of water. The reaction mixture is cooled with an ice bath, and then acidified to pH 2 with 0.5 N HCl. The product which precipitates is taken up in ether, the organic phase is rinsed with water, dried with Na$_2$SO$_4$, and then evaporated to dryness to produce the saponified phosphinic block, with a 95% yield.

4) Preparation of the Fmoc-Phe(PO(Ad)—CH$_2$)AlaOH block.

To a methanol solution (Rml), containing the Z-Phe(PO(Ad)—CH$_2$)AlaOH phosphinic block (1 mmol) and ammonium formiate (4 mmol) 0.25 g of 10% Pd/C is added. After 12 minutes at ambient temperature, the catalyst is eliminated by filtration on cellite, and the residue is then dried in a vacuum to dryness. Said residue is taken up in dichloromethane, and then evaporated to dryness. This procedure is repeated several times. Said residue is treated with chloroform and the excess ammonium formiate which has not reacted and is present in precipitate form, is eliminated by filtration. The product formed is taken up in Na$_2$CO$_3$ (3 ml). The reaction mixture is evaporated by one-half in a vacuum, and 1.5 ml of water and 2 ml of dioxane are then added. An Fmoc-Cl (1.2 mmol) solution in dioxane (2 ml) is added to the reaction mixture, cooled in an ice bath. This solution is left under stirring for 2 hours at 4° C., followed by 4 hours at ambient temperature. The reaction mixture is diluted with 20 ml of water, cooled with an ice bath and acidified to pH 2 with 2N HCl. The product which precipitates is taken up rapidly in ether. This organic phase is rinsed with water, dried with Na$_2$SO$_4$, and then evaporated in a vacuum to dryness to produce the required product, which is purified by flash chromatography (chloroform/methanol, 9.5:0.5) with a final yield of 65%.

b) Phosphinic peptide synthesis.

For the phosphinic peptide synthesis, the first amino acid Xaa is attached to 2-chlorotrityl resin using the technique by Barbos et al described in G. Int. J. Pept. Protein., Res, 1991, 37, 513–520 [11]. The phosphinic block is then fixed onto said first amino acid followed by the Xaa' amino acids. The Fmoc group is eliminated with 30% piperidine in N-methylpyrrolidone and the subsequent Xaa' residues are linked using the 2-(1H)benzotriazol-1-yl)-1,1,3,3-tetramethyluronium hexafluorophosphate/diisopropyl ethyl amine. In this process, the different steps are performed with conventional techniques using the reagents and solvents generally used in peptide chemistry, as described in Yiotakis et al, J. Org. Chem (1996) 61, 6601–6605, [10].

In this way, peptide mixtures comprising 20 different amino acids in the Xaa position and 20 different amino acids in the Xaa' position, the peptide mixtures being separated and identified according to the type of amino acid in the Xaa position.

Said mixtures were evaluated at final peptide concentrations of 200 nM in order to determine their ACE inhibitory capacity. To assay ACE, a new quenched fluorescence ACE substrate (Mca-Ala-Ser-Asp-Lys-Dpa) was developed, where Mca represents methoxy coumarine and Dpa 2-(N-dinitrophenyl)aminopropionic acid. Said substrate, which is only fluorescent when intact, emits an intense fluorescent signal after splitting, between the Asp and Lys residues, by ACE. Using this type of substrate, it is possible to test the inhibitory power of a very large number of compounds in Elisa plates.

The inhibitory power of the compounds is determined in a conventional competition test based on the breakdown of the quenched fluorescence substrate Mca-Ala-Asp-Ser-Lys-Pro. The breakdown of said substrate by ACE results in the observation of a fluorescent signal at 400 nm, when the sample is excited at 328 nm. The inhibition experiments are conducted in Elisa plate wells, in volumes of 200 $\mu$l of buffer: pH 6.8, 50 mM Hepes, 200 mM NaCl, 1 mM $ZnCl_2$, at 25° C., in a Dynatech Fluorolite 1000 type unit. The concentration of the substrate in a typical experiment is 20 $\mu$M. For the inhibition experiments, the inhibitor is placed in the presence of the enzyme for 45 min, and the reaction is then initiated by simply adding a very small volume of substrate. The inhibition percentages are calculated from the initial rate variations in the presence of inhibitor. The breakdown kinetics were determined from the record of the fluorescence variations over a 40 min time interval.

The inhibitory activity of each mixture was evaluated on two mutant forms of ACE: the N-terminal form, wherein the C-terminal site is rendered inactive by mutagenesis and the C-terminal form comprising an inactive N-terminal site, as described by Wei et al, in J. Biol. Chem. (1992) 267, 13398–13405, [14]. Said mutants were produced from CHO cells.

Figure 2:
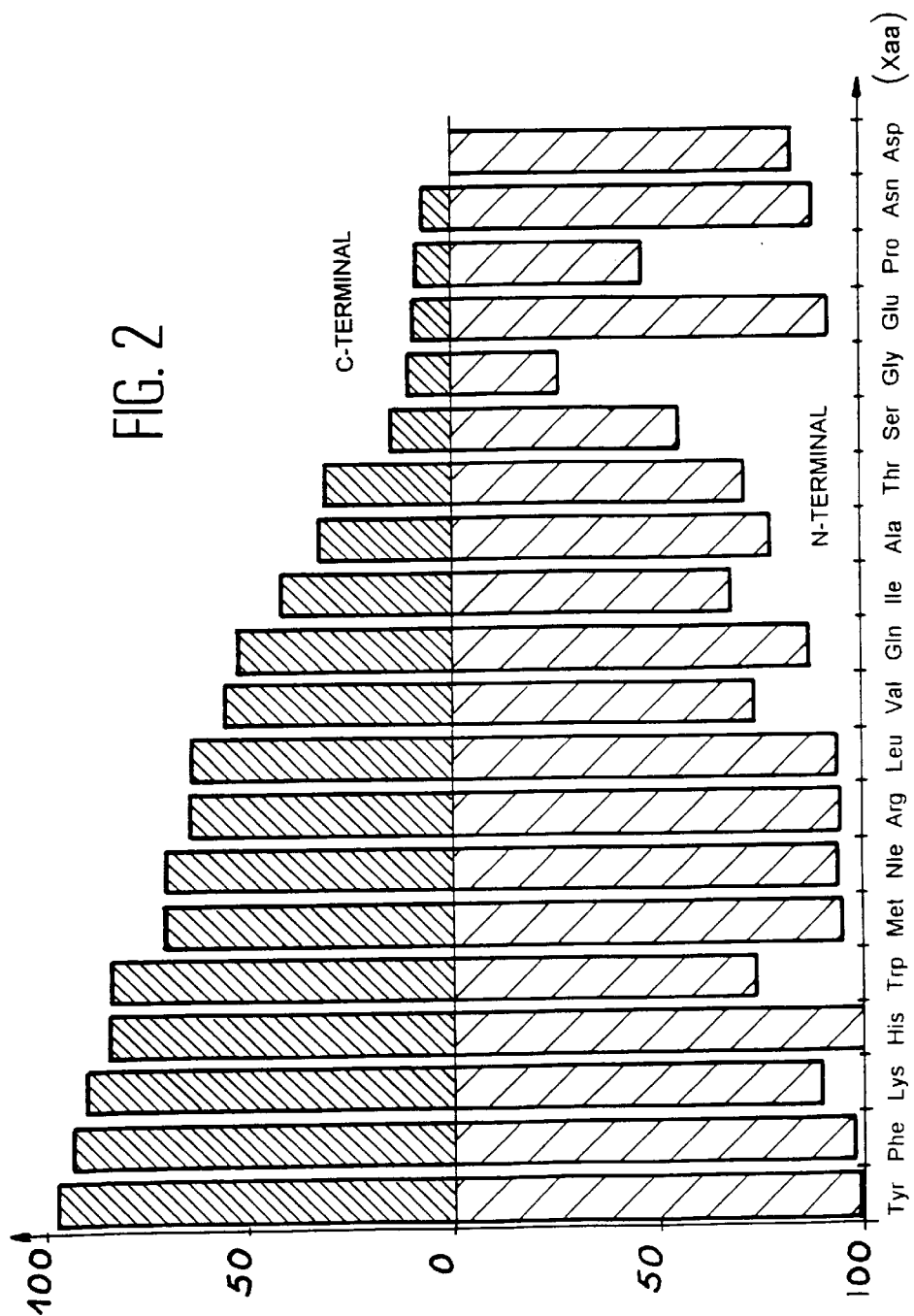
FIG. 2 illustrates the inhibition percentages with respect to the C-terminal site and N-terminal site of human angiotensin-converting enzyme, of different peptide mixtures.

In FIG. 2, the inhibition percentages observed with the N- and C-terminal mutants of ACE as a function of the type of amino acid present in the Xaa position of the inhibitors are given. This figure demonstrates that a very large number of substitutions are compatible for inhibition of both the N-terminal and C-terminal site of ACE. However, in terms of selectivity, it is noted that only the presence of an aspartic residue in the Xaa position enables the inhibition of the N-terminal site, while it renders the mixture of inhibitors comprising this residue inactive with respect to the C-terminal site of ACE.

These results thus demonstrate that it is essential to have an Asp residue in the Xaa position to obtain a selective N-terminal site inhibitor.

EXAMPLE 2

On the basis of the results of example 1, according to same procedure as in example 1 twenty phosphinic peptides according to the general formula Ac-Asp-Phe$\Psi(PO_2CH_2)$-Ala-Xaa'-$NH_2$, wherein the Xaa' position is occupied by a single amino acid, were synthesised. Said peptides were tested as in example 1 to determine their inhibitory activity on the N-terminal and C-terminal sites of ACE.

Figure 3:
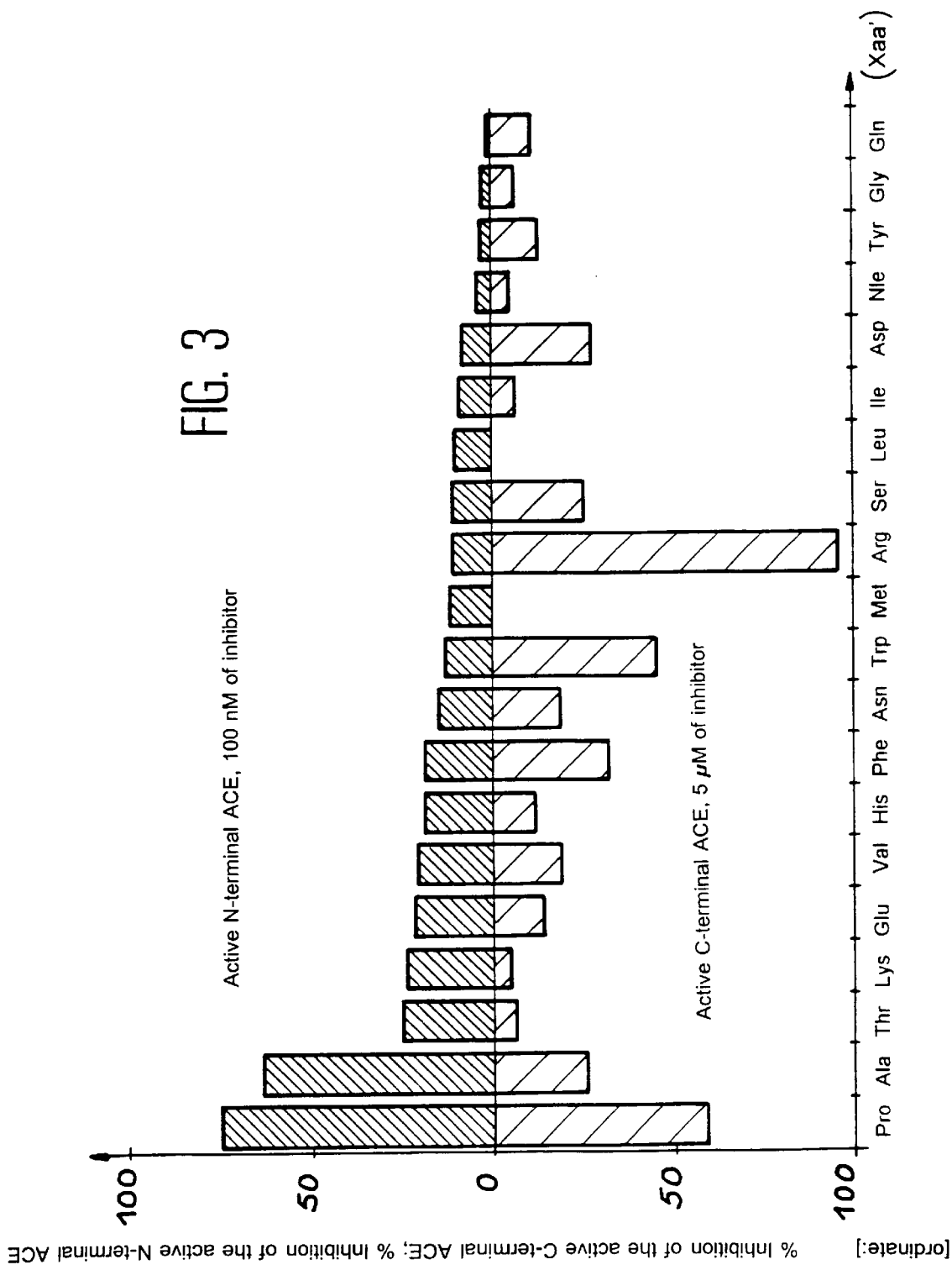
FIG. 3 illustrates the inhibition percentages with respect to the C-terminal site and N-terminal site of various peptide derivatives.

The results obtained are represented in FIG. 3 which illustrates the inhibition percentages of said peptides on the N and C-terminal sites of ACE as a function of the type of residue in the Xaa' position.

It is important to note that, for the N-terminal site, the inhibitors were studied at a concentration of 100 nM, while, for the C-terminal site, the concentration used to observe a noteworthy inhibition was set at 5 $\mu$M. Said difference in concentration reflects the better affinity of these compounds for the N-terminal site of ACE.

In FIG. 3, it is observed that the presence in the Xaa' position of proline and alanine residue peptides makes it possible to improve the degree of selectivity in favour of the N-terminal site and that the activity of the Thr, Lys,, Met and Leu residues is very low on the C-terminal site of the enzyme.

EXAMPLE 3

In this example, the inhibition constants Ki of the Ac-Asp-Phe$\Psi(PO_2CH_2)$Ala-Xaa'-$NH_2$ compound obtained in example 2 were determined, with respect to the N- and C-terminal mutants of ACE. The results obtained are given in table I.

According to this data, it is observed that said peptide is more active by three orders of magnitude with respect to the N-terminal site of ACE than its C-terminal site.

EXAMPLE 4

In this example, four analogues of the peptide in example 3 with different terminal groups were synthesised and the effect of the N- and C-terminal groups on the selectivity with respect to the N-terminal site of ACE was determined using the same procedure as in example 1. The results are given in table II.

The results of table II show that the presence of the carboxamide group is essential for the selectivity of the molecule. Indeed, while the presence of carboxylate group reinforces affinity with respect to the N-terminal site, this modification induces a loss of selectivity, since this new compound is very active in the C-terminal domain. To a lesser degree, it is seen that the presence of the N-acetyl group also plays a role in selectivity. The last analogue reveals the very important role of the aspartic residue in the N-terminal position in selectivity.

EXAMPLE 5

In this example, the effect of the configuration of the Phe and Ala residues surrounding the phosphinic block with respect to the affinity of the peptide derivative in example 3 for: the N-terminal site was studied.

The synthesis of the Ac-Asp-Phe$\Psi(PO_2CH_2)$Ala-Ala-$NH_2$ peptide results in a mixture of four diastereoisomers, due to the presence of two asymmetric centres in said compound. The reverse phase HPLC high performance liquid chromatography purification of this product on a Spectra System VYDAC analytical C18 column ($\lambda$=220 nm, flow rate=1 ml/min) is used to separate three fractions.

Figure 4:
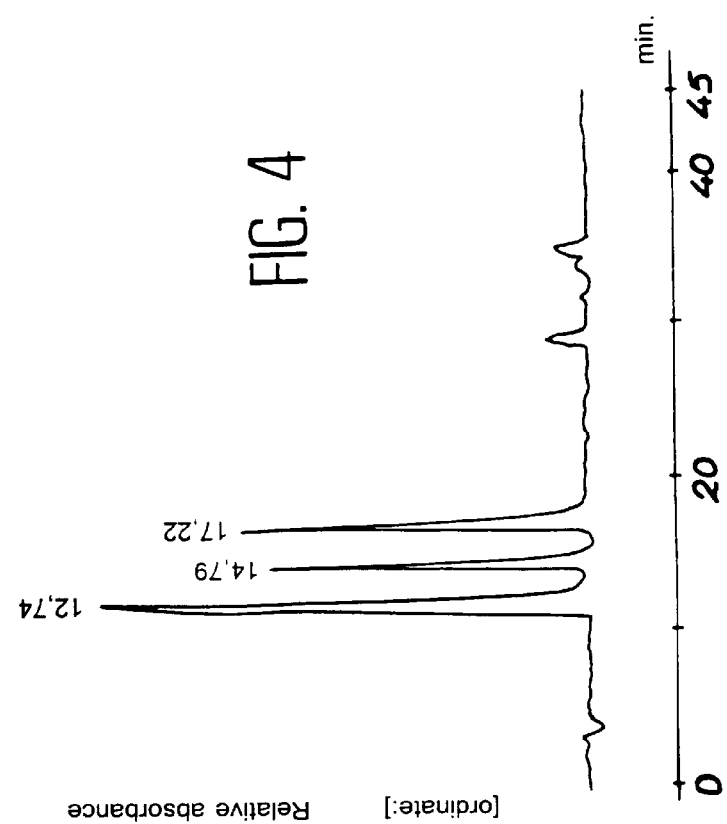
FIG. 4 in a chromatogram obtained by reverse phase HPLC of a mixture of diastereoisomers of the peptide derivative Ac-Asp-PheΨ(PO$_2$CH$_2$)-Ala-Ala-NH$_2$ according to the invention.

FIG. 4 illustrates the chromatogram obtained which comprises three peaks.

On the basis of the intensity of the HPLC peaks and the NMR spectrum of phosphorus, it is demonstrated that the first peak contains two diastereoisomers, the other two peaks containing only one diastereoisomer. The determination of the activity of these fractions shows that only the first fraction contains active compounds.

EXAMPLE 6

Since the purification method in example 5 does not enable the separation of the two diastereoisomers present in the fraction corresponding to the first peak, the Ac-Asp-Phe-Ψ(PO₂CH₂)-Ala-AlaNH₂ peptide is synthesised from an R configuration phenylaminophosphinic residue to obtain, at the end of synthesis, a mixture of two diastereoisomers that can be easily separated by reverse phase HPLC.

To synthesise the peptide containing the R configuration aminophenylphosphinic residue, the racemic of said aminophenylphosphinic acid is synthesised, and the isomers are separated by recrystallisation in the presence of a chiral amine, according to the method described by Baylis et al., in J. Chem. Soc. Perkin. Trans (1984) 2845–2849 [15]. In this way, optically pure R and S configuration aminophenylphosphinic acid residues are obtained. Using the R configuration acid, the Fmoc$_{(R)}$Phe(PO(Ad)—CH₂)AlaOH as in example 1 to obtain a mixture of two diastereoisomers Ac-Asp-$_{(R)}$Phe(PO₂CH₂)$_{(R)}$Ala-Ala-NH₂

Ac-Asp-$_{(R)}$Phe(PO₂CH₂)$_{(S)}$Ala-Ala-NH₂ which is separated by C18 reverse phase HPLC.

The Ac-Asp-PheΨ(PO₂CH₂)Ala-Ala-NH₂ peptide is synthesised using a conventional solid phase synthesis strategy, by Fmoc chemistry, using Rink amide resin as the solid substrate. The synthesis of said peptide is performed by successively linking the following blocks: Fmoc-Ala, Fmoc-Phe(PO(Ad)—CH₂)AlaOH and Fmoc-Asp(t-Bu). The links were produced with-the on-site strategy using 2-(1Hbenzotriazol-1-yl)1,1,3,3-tetramethyluronium-hexafluorophosphate/diisopropylethylamine. The linking conditions are as follows: three Fmoc derivative equivalents and 4 diisopropylethylamine equivalents in dimethylformamide are added to the resin and left to react for 30 minutes. To split the Fmoc group, the following conditions were used: 50% piperidine in dimethylformamide, for 30 minutes. The splitting of the peptide from the resin and of the protective groups are performed by treating with a trifluoroacetic acid solution containing 2.5% water, 2.5% thioanisol, 2.5 M phenol, 1.25% ethanedithiol and 1.25% triisopropylsilane. The product was purified by C-18 reverse phase HPLC.

Figure 5:
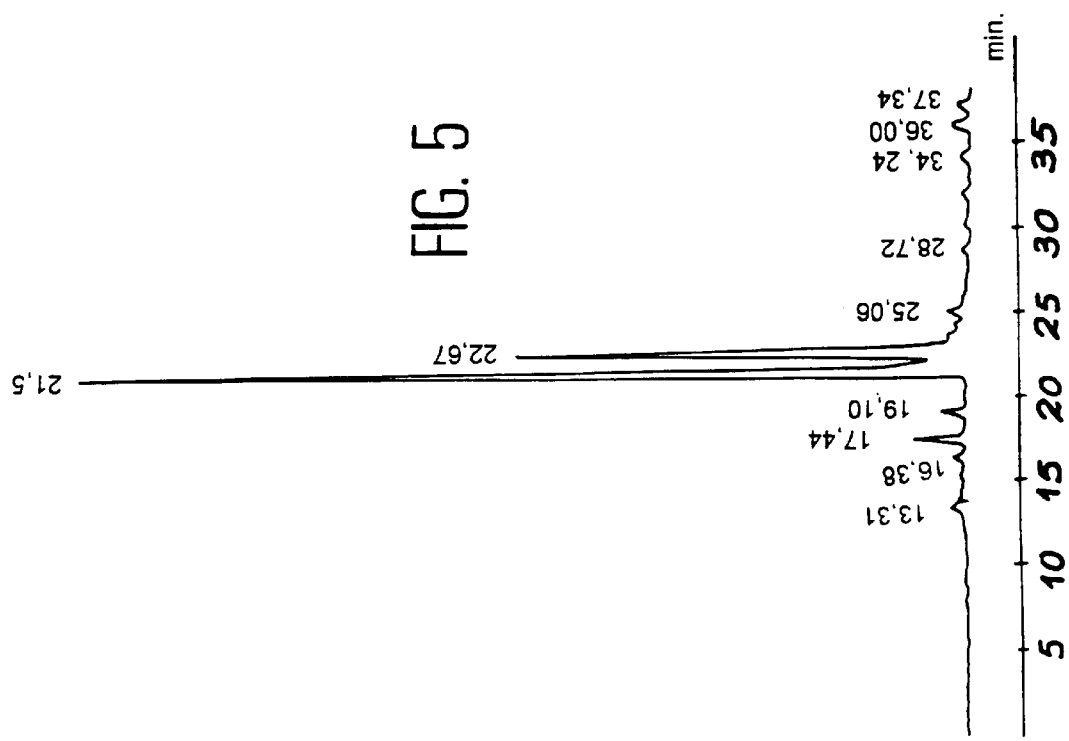
FIG. 5 is a reverse phase HPLC chromatogram of the mixture of two diastereoisomers of the peptide derivative Ac-Asp-PheΨ(PO$_2$CH$_2$)Ala-Ala-NH$_2$ according to the invention.

FIG. 5 illustrates the chromatogram obtained under these conditions which comprises two peaks, only one of which, the first, has an inhibitory power on ACE. The active peak contains a molecule characterised by a Ki of 12 nM on the N-terminal site and by a Ki of 25 μM on the C-terminal site of ACE.

The most active fraction of the peptide contains an S configuration pseudo-alanine residue. Therefore, the active structure of the peptide is as follows: Ac-Asp-$_{(R)}$Phe(PO₂CH₂)-$_{(S)}$Ala-Ala-NH₂ III, hereafter referred to as RXP 407. The inhibition constants of this optically pure compound are given in table III.

The purity of the RXP 407 compound was established by mass spectrometry (theoretical mass 498.5, exp mass 498) and by magnetic resonance of phosphorus, the proton and carbon 13.

Phosphorus spectrum: d=40.78 ppm, reference phosphoric acid (0 ppm)

Proton spectrum (ppm): Asp: Ha, 4.28, Hb,b', 2.0 and 2.28, Phe: Ha, 4.08, Hb,b', 2.55 and 3.10, Ar, 7.13 and 7.22; Ala: Ha, 2.58, Hb, 1.08; Ala: Ha, 4.12, Hb, 1.28; P—CH2, 1.48 and 1.62; CH3—CO, 1.82, reference TSP (0 ppm).

Carbon 13 spectrum (ppm): Asp: Ca, 55.3, Cb, 41.5, CO, 180.5; Phe: Ca, 54.5, Cb, 36, Ar, 129.8, 131.7, 132.5, 141.2; Ala: Ca, 37.6, Cb, 21.4, CO, 182.3; Ala: Ca, 53, Cb, 19.6, CO, 181.5; CH2—P, 34.4; CH3—CO, 24.5 and 177, reference TSP (0 ppm).

The spectra were determined in D₂O, on a Bruker DRX type unit, operating at a frequency of 250 MHz for the proton, 101 MHz for phosphorus and 62 MHz for carbon. The attributions were carried out using COSY, TOCSY, HMQC and HMBC type two-dimensional experiments.

The RXP 407 compound is of great interest since it is able to discriminate between the two active sites of ACE. This compound is a strong inhibitor of the N-terminal site of ACE (Ki=12 nM), but has a very low affinity for the C-terminal site (Ki=25 μM). In addition to this property, it is important to note that this molecule, given the Asp and pseudo-Phe residues, involves, during its interaction, the S₁ and S₂ sub-sites of ACE, which is an unusual property for an ACE inhibitor. Even more surprisingly, said molecule comprises, in the C-terminal position of its structure, a carboxamide group, while all the ACE inhibitors described to date systematically have a free carboxylate group. In this way, said molecule appears to be very original both in terms of its chemical structure and its inhibitory activity.

EXAMPLE 7

In this example, the RXP 407 peptide is used as a natural ACE inhibitor, and the effect of the RXP 407 concentration (in nM) on the ACE inhibition percentage is studied.

The inhibitory power of the compound is determined as in example 1 using wild human ACE produced by CHO cells according to the protocol described in the reference Wei et al, J. Biol. Chem. (1992) 267, 13398–13405 [14].

Figure 6:
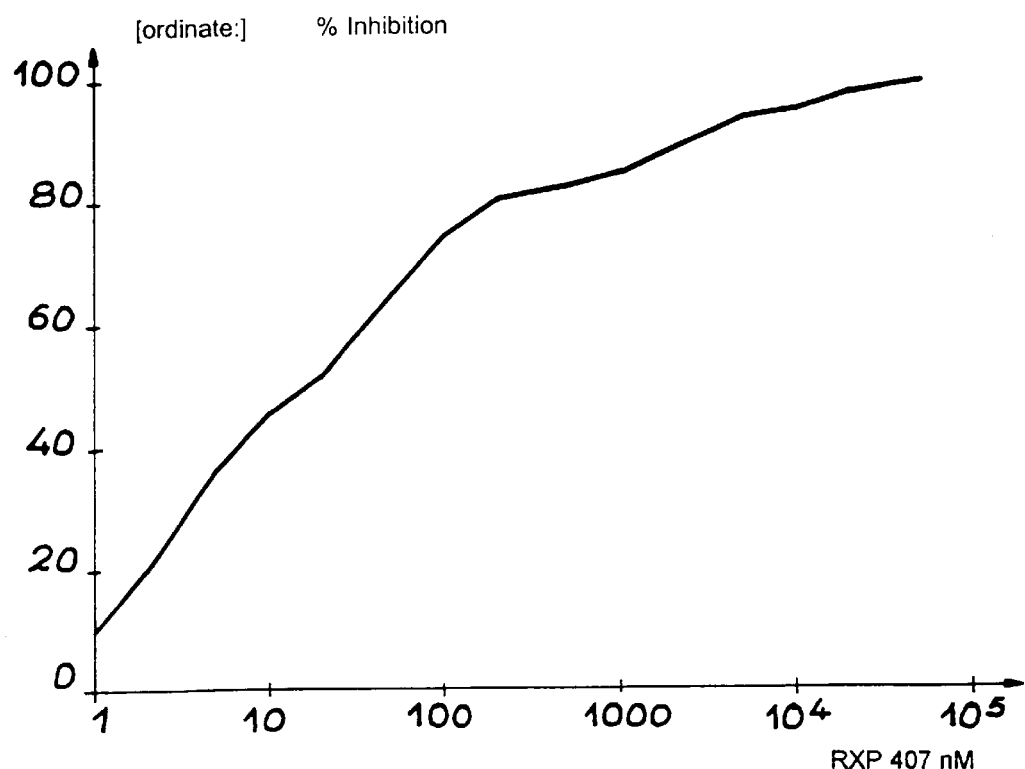
FIG. 6 illustrates the inhibition percentage obtained by the peptide derivative RXP 407 as a function of the concentration used.

The results obtained are represented in FIG. 6 which illustrates the inhibition profile that can be obtained with RXP 407 for natural ACE inhibition. The presence of two levels in the inhibition curve conveys the existence of two active sites in natural ACE, the left part of the curve being due to the inhibition of the N-terminal domain of ACE, the right part being due to that of the C-terminal domain. The inflection points appearing on this curve indicate the IC50 values of RXP 407 with respect to the N and C-terminal sites of natural ACE which are compatible with the Ki values measured using the ACE mutants.

This experiment demonstrates that RXP 407 indeed behaves like a selective inhibitor of the N-terminal domain of the natural enzyme. It is interesting to note that the shape of the curve is due to the fact that the substrate used in this experiment is equally split by the N-terminal and C-terminal domains.

In this way, it is possible to use RXP 407 to identify substrates which would be split by only one of the two active sites of the enzyme. Indeed, for a substrate only split by one of the two sites, the inhibition curve will contain only one level and not two. If the substrate is only split by the N-terminal domain, the inflection point of the curve will be located at around the RXP 407 concentration of 100 nM, while for a substrate only split by the C-terminal domain, the inflection point will be shifted to 10 mM.

In this way, this new inhibitor is a very good tool for studying the selectivity of natural ACE with respect to the breakdown of physiological substrates.

EXAMPLE 8

In this example, the pharmacokinetics and the metabolism of the RXP 407 compound is studied in animals.

For this purpose, an RXP 407 comprising three tritium atoms on the N-acetyl group is synthesised to be able to conduct a study on the pharmacokinetics and metabolism of said molecule in rats, by injecting said product at doses of 0.1, 1 and 5 mg/kg by intravenous bolus.

The plasma concentration of RXP 407 as a function of time is then determined.

Figure 7:
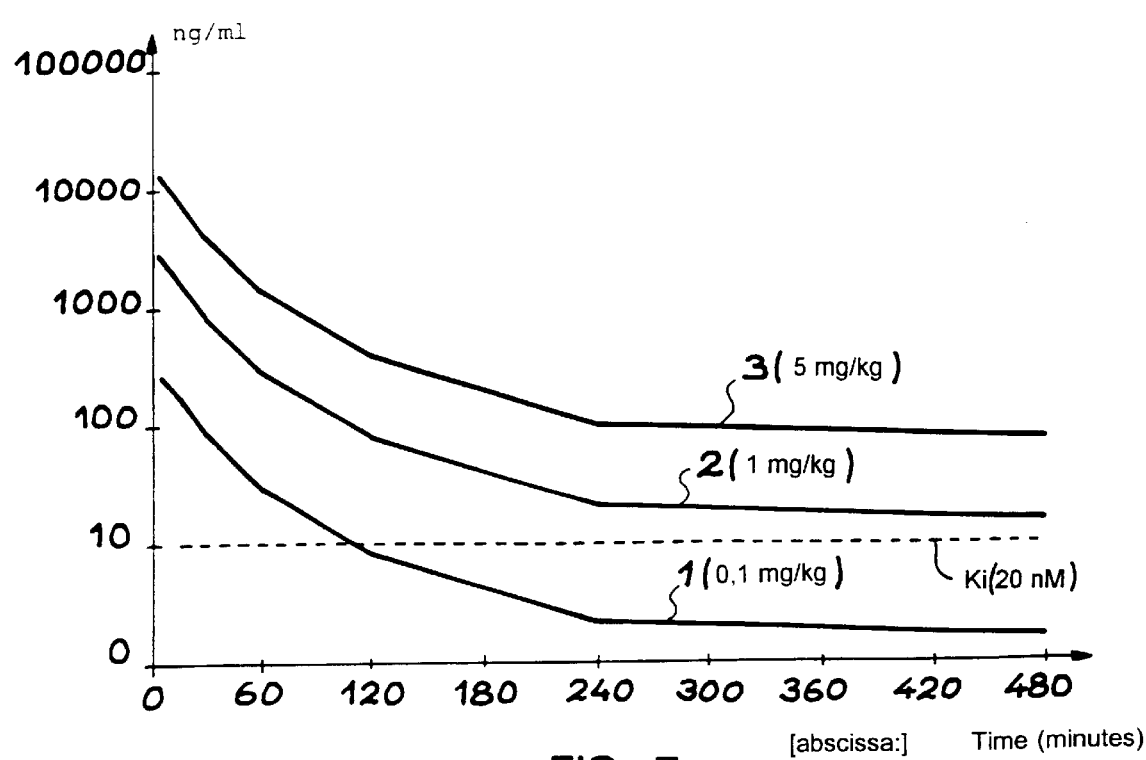
FIG. 7 illustrates the variation as a function of time of the plasma concentration of a peptide derivative according to the invention in rats.

The results obtained are represented in FIG. 7. Curve 1 corresponds to 0.1 mg/kg, curve 2 to 1 mg/kg and curve 3 to 5 mg/kg. The dotted curve illustrates the Ki of RXP 407 (20 nM).

In this way, it is observed that the injection of one 5 mg/kg dose by intravenous bolus induces plasma RXP 407 concentrations of 100 ng/ml of product for over four hours, which is equivalent to a concentration equal to 10 times the Ki of said inhibitor for the N-terminal site.

Table IV contains the results obtained for the elimination of tritiated RXP 407 in vivo in rats. These results are expressed as a % of the injected radioactivity. They demonstrate that the compound is essentially eliminated in urine (87% after 24 hours), and to a much lesser extent in faeces (13%). No trace of this product is detected in the airways.

According to this table, it can be seen that the 4 rats eliminated 100% (100.09±7) of the RXP 407 injected in 48 hours. The majority of the product is essentially eliminated in urine, to a much lesser extent in faeces, and practically not at all via the airways.

In addition, the analysis of the structure of the product in urine and faeces demonstrates that the RXP 407 does not undergo any metabolism.

The toxicity of this product was evaluated in mice. In this way, it was checked that said product did not induce any signs of toxicity in mice, at a dose of 25 mg/kg. After 7 days of observation, the treated mice were living completely normally.

In this way, RXP 407 is an effective inhibitor. The interest of this new ACE inhibitor lies in the fact that it represents the first selective inhibitor of the N-terminal site of this enzyme. The pharmacodynamic properties, the absence of a metabolism and therefore stability in vivo make it an ideal product for, in therapeutic protocols, inhibiting the N-terminal site of ACE without affecting the physiological functions controlled by the C-terminal site of the enzyme.

In addition, RXP 407 makes it possible to establish in vivo the respective contribution of the N-terminal and C-terminal sites of ACE in the metabolism of Ac-Ser-Asp-Lys-Pro. The experiments conducted in vitro demonstrate that the N-terminal site of ACE is much more effective for splitting said peptide than the C-terminal site; therefore, controlling the metabolism via RXP 407 is a reasonable objective.

EXAMPLE 9

In this example, the effect of injecting RPX 407 in vivo in mice is studied.

For this purpose, the mice undergo an infusion of RXP 407 for 30 minutes, at doses of 0.1, 1 and 10 mg/kg and the Ac-Ser-Asp-Lys-Pro-(Ac-SDKP) peptide concentration of the mouse plasma is determined.

The Ac-Ser-Asp-Lys-Pro is determined by a competition immunoenzyme assay using polyclonal antibodies and Ac-SDKP linked to Electrophorus Electricus acetyicholinesterase.

The same plasma Ac-SDKP measurements are made on mice infused with Lisinopril of a 10 mg/kg dose and on non-infused control mice. Lisinopril is an inhibitor used in clinical practice which inhibits both active sites of ACE non-selectively.

Figure 8:
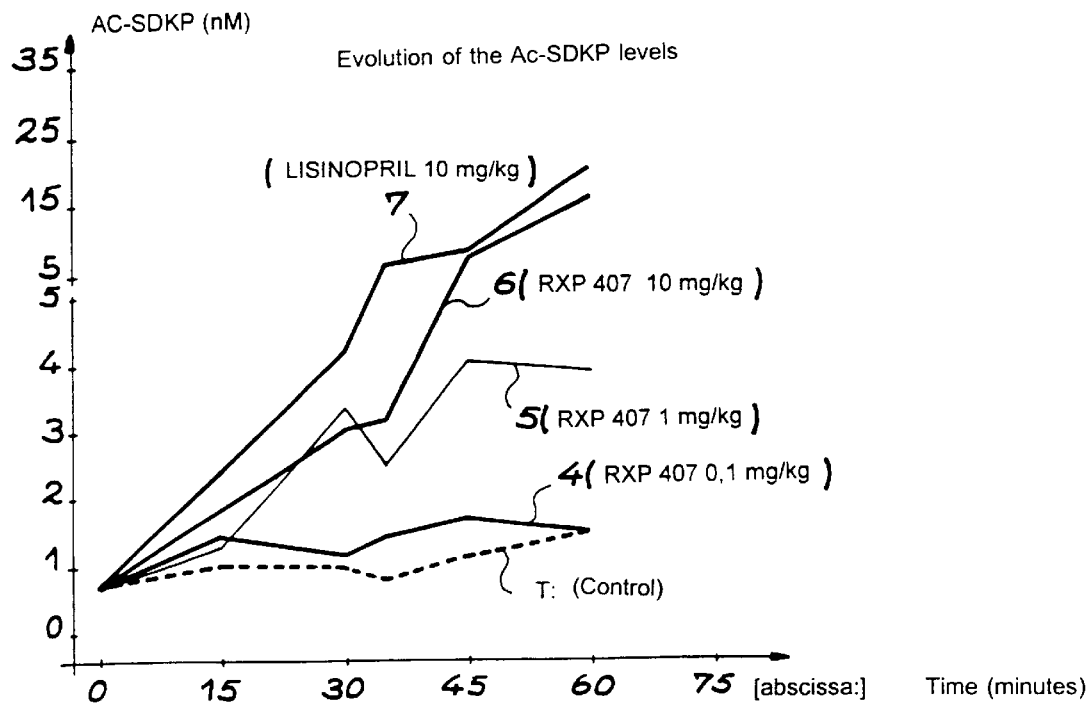
FIG. 8 illustrates the variation as a function of time of the plasma concentration of Ac-Ser-Asp-Lys-Pro peptide in mice infused with the inhibitor according to the invention RXP 407 at 0.1, 1 and 10 mg/kg doses (curves 4, 5 and 6), in mice infused with Lisinopril at a 10 mg/kg dose (curve 7) and non-infused control mice (curve T).

FIG. 8 illustrates the results obtained, i.e. the Ac-SDKP concentration (nM) as a function of time (in minutes).

Curves 4, 5 and 6 relate to mice infused with RXP 407 at doses of 0.1 mg/kg (curve 4), 1 mg/kg (curve 5) and 10 mg/kg (curve 6).

Curve 7 relates to mice infused with 10 mg/kg of Lisinopril.

Curve T relates to the control mice. It is observed that the injection of RXP 407 induces a very significant increase in the plasma level of Ac-SDKP peptide. Compared to a non-selective inhibitor of both active sites of ACE, it is noted that the Ac-SDKP levels in the plasma are the same as those obtained with RXP 407. Given that RXP 407 only inhibits one of the two ACE sites, the N-terminal, it is possible to conclude from these experiments that the C-terminal site of ACE is not involved in the metabolism of Ac-SDKP and that, on the other hand, said metabolism only depends on the N-terminal site of ACE, hence the interest of using RXP 407, compared to conventional ACE inhibitors, which inhibit both ACE sites non-selectively. This experiment also demonstrates the effective in vivo activity of RXP 407.

EXAMPLE 10

In this example, the effect of RXP 407 on the levels of renin, another enzyme involved in arterial pressure regulation, is determined. Inhibition of ACE with a conventional inhibitor of said enzyme stops the hydrolysis of angiotensin I into angiotensin II. Angiotensin is indeed one of the physiological substrates of ACE. The decrease in the angiotensin II level in plasma by a retrocontrol mechanism, increases the plasma level of renin, an enzyme directly involved in the production of angiotensin I, from angiotensinogen.

In this way, the inhibition of ACE may be monitored indirectly by the plasma renin level.

This level may be evaluated by the capacity of renin in plasma samples to hydrolyse excess angiotensinogen present in mouse plasma. The formation of angiotensin I is then measured by a radioimmunological assay and the renin level is expressed in ng of angiotensin I formed per ml of plasma and per hour of incubation.

Figure 9:
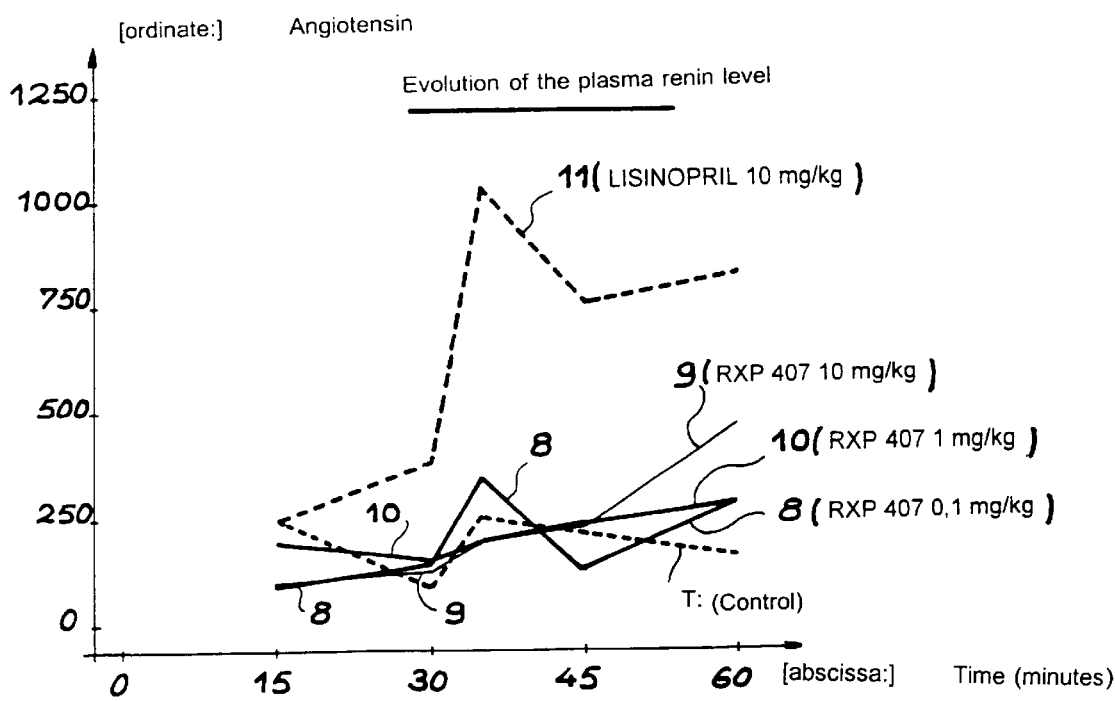
FIG. 9 illustrates the variation as a function of time of the plasma concentration of angiotensin I (ng/ml/h) in mice infused with RXP 407 at 0.1, 1 and 10 mg/kg doses (curves 8, 9 and 10), in mice infused with 10 mg/kg of Lisonopril (curve 11), and in non-infused mice (curve T).

The results obtained are given in FIG. 9 for:

mice infused with RXP 407 at doses of 0.1 mg/kg (curve 8), 1 mg/kg (curve 9) and 10 mg/kg (curve 10).

mice infused with Linisopril at a dose of 10 mg/kg (curve 11), and control mice (curve T).

FIG. 9 shows that treatment of a mouse with Lisinopril induces an increase in the plasma renin level, which agrees with the ACE inhibition effect with this compound. However, it is demonstrated that treatment with RXP 407 does not induce an increase in renin. In this way, this inhibitor makes it possible to selectively inhibit the breakdown of Ac-SDKP peptide, without affecting arterial pressure regulation. This observation, very important in terms of the selectivity of the activity in vivo of the RXP 407 compound, suggests that only the C-terminal site of ACE is involved in the hydrolysis of angiotensin I, thus explaining why injecting RXP 407 has no effect on renin levels.

In this way, all these, experiments confirm the interest of the use of RXP 407 to control plasma levels of Ac-SDKP peptide. It is reminded that it was demonstrated that said peptide had a protective effect on bone marrow strain cells during chemotherapy and radiotherapy protocols. Therefore, RXP 407 will be very useful in this context, by mobilising the physiological levels of Ac-SDKP peptide, via the inhibition of its metabolism with ACE.

Since the peptide Ac-Ser-Asp-Lys-Pro peptide is a haematopoiesis regulator, it is possible to propose using the inhibitor according to the invention in anti-cancer chemotherapy or radiotherapy protocols, in order to protect bone marrow cells against the toxic effects of the cancer treatment. It is also possible to envisage an application in the field of cancer treatment since the effect of ACE on the proliferation different cell types via-the activity of its N-terminal domain can still be envisaged.

Another consequence of said inhibitor is that it represents a very effective tool for studying the respective contribution of N- and C-terminal sites of wild ACE in the breakdown of different physiological substrates of said enzyme.

REFERENCES QUOTED

[1]: Soubrier et al, Proc. Natl. Acad. Sci. USA (1988) 85, 9386–9390.
[2]: Lenfant et al, Proc. Natl. Acad. Sci. USA (1989), 86, 779–782.
[3]: Lombard et al, Cell. Tissue. Kinet (1990) 23, 99–103.
[4]: Bodgen et al, Ann. N.Y. Acad. Sci. (1991) 628, 126–139.
[5]: Rousseau et al, J. Biol. Chem. (1995) 270, 3656–3661.
[6]: Azizi et al, J. Clin. Invest. (1996) 97, 839–844.
[7]: Volpert et al, J. Clin. Invest. (1996) 98, 671–679.
[8]: FR-A-2 676 059.
[9]: EP-A-0 725 075.
[10]: Yiotakis et al in J. Org. Chem., 1996, 61, 6601–6605.
[11]: Barlos et al, G. Int. J. Pept. Protein. Res, 1991, 37, 513–520.
[12]: Jiracek et al, J. Biol. Chem. (1995) 270, 21701–21706.
[13]: Jiracek Yiotakis et al, J. Biol. Chem. (1996) 271, 19606–16661.
[14]: Wei et al, in J. Biol. Chem. (1992) 267, 13398–13405.
[15]: Baylis et al., in J. Chem. Soc. Perkin. Trans (1984) 2845–2849.

TABLE I

|  | Ki of compound Ac-Asp-PheΨ (PO$_2$CH$_2$) Ala-AlaNH$_2$ |
| --- | --- |
| Active N-terminal ACE | 25 nM |
| Active C-terminal ACE | 25 μM |

TABLE II

|  | Ki Active N-terminal ACE | KI Active C-terminal ACE |
| --- | --- | --- |
| Ac-Asp-PheΨ (PO$_2$CH$_2$) Ala-AlaNH$_2$ | 25 nM | 25 μM |
| Ac-Asp-PheΨ (PO$_2$CH$_2$) Ala-AlaOH | 2 nM | 7 nm |
| H$_2$N-Asp-PheΨ (PO$_2$CH$_2$) Ala-AlaNH$_2$ | 5 nM | 800 nM |
| H$_2$N-Asp-PheΨ (PO$_2$CH$_2$) Ala-AlaOH | 2 nM | 60 nM |
| Ac-Ala-PheΨ (PO$_2$CH$_2$) Ala-AlaNH$_2$ | 15 nM | 200 nM |

TABLE III

|  | KI Active N-terminal ACE | Active C-terminal ACE |
| --- | --- | --- |
| Ac-Asp-$_{(R)}$PheΨ (PO$_2$CH$_2$)$_{(S)}$ Ala-AlaNH$_2$ | 12 nM | 25 μM |

TABLE IV

| | (% of injected radioactivity) | | | | | | | | | | |
| --- | --- | --- | --- | --- | --- | --- | --- | --- | --- | --- | --- |
| | Urine | | | | Faeces | | Expired air | | | | |
| Rat | 4 h | 8 h | 24 h | 48 h | 24 h | 48 h | 4 h | 8 h | 24 h | 48 h | Total |
| 1 | 0 | 89.79 | 6.71 | 0.59 | 2.70 | 1.83 | 0 | 0 | 0.01 | 0 | 101.80 |
| 2 | 45.14 | 20.77 | 4.24 | 1.23 | 6.69 | 19.32 | 0 | 0 | 0.02 | 0 | 98.96 |
| 3 | 68.84 | 6.30 | 2.19 | 0.87 | 6.02 | 4.94 | 0 | 0 | 0.02 | 0.01 | 93.20 |
| 4 | 0 | 81.27 | 5.19 | 0.86 | 8.58 | 3.93 | 0 | 0 | 0.01 | 0 | 106.49 |
| Mean for 4 rats | 28.49 | 49.53 | 4.58 | 0.89 | 6.00 | 7.51 | 0 | 0 | 0.02 | 0 | 100.09±7 |

What is claimed is:

1. A peptide derivative comprising the amino acid sequence according to the following formula:

-Asp-PheΨ(PO$_2$CH$_2$)-Ala-Xaa'-     (I)

wherein:
Ψ(PO$_2$CH$_2$) indicates that the peptide bond (CONH) between Phe and Ala has been replaced by the phosphonic bond PO$_2$CH$_2$, and
Xaa' represents an amino acid residue.

2. The peptide derivative according to claim 1, wherein Xaa' represents Ala.

3. The peptide derivative according to claim 1, wherein the Phe residue has an R configuration.

4. The peptide derivative according to claim 1, wherein the Ala residue has an S configuration.

5. A pharmaceutical formulation comprising a peptide derivative according to claim 1.

6. The pharmaceutical formulation according to claim 5 in a form suitable to protect haematopoietic strain cells of a patient undergoing aggressive chemotherapy or radiotherapy treatment.

7. The pharmaceutical formulation according to claim 5 in a form suitable for use in cancer treatment.

8. A method for inhibiting the N-terminal site of human angiotensin-converting enzyme in a patient comprising
administering an amount of the peptide derivative of claim 1 effective to inhibit human angiotensin-converting enzyme to said patient, thereby inhibiting the N-terminal site of human angiotensin-converting enzyme.

9. The method of claim 8, wherein said inhibiting further comprises regulating the proliferation of haematopoietic strain cells in a patient undergoing cancer treatment.

10. A method for inhibiting human angiotensin-converting enzyme comprising administering an effective amount of the peptide of claim 1 to a subject in need thereof.

11. The method of claim 10 that comprises administering said peptide to a subject undergoing aggressive chemotherapy.

12. The method of claim 10, that comprises administering said peptide to a subject undergoing radiotherapy.

13. A peptide derivative having the formula:

$$R^1\text{-Asp-Phe}\Psi(PO_2CH_2)\text{-Ala-Xaa'-NH}_2 \quad (II)$$

wherein:

R$^1$ represents the acetyl or benzyloxycarbonyl group,

-$\Psi(PO_2CH_2$ indicates that the peptide bond (CONH) between Phe and Ala has been replaced by the phosphonic bond $PO_2CH_2$, and -Xaa' represents an amino acid residue.

14. The peptide derivative according to claim 13, wherein R$^1$ represents the acetyl group.

15. The peptide derivative according to claim 13, wherein Xaa' represents Ala.

16. The peptide derivative according to claim 13, wherein the Phe residue has an R configuration.

17. The peptide derivative according to claim 13, wherein the Ala residue has an S configuration.

18. A pharmaceutical formulation comprising a peptide derivative according to claim 13.

19. The pharmaceutical formulation according to claim 18 in a form suitable to protect haematopoietic strain cells of patient undergoing aggressive chemotherapy or radiotherapy treatment.

20. A method for inhibiting the N-terminal site of human angiotensin-converting enzyme in a patient comprising
administering an amount of the peptide derivative of claim 13 effective to inhibit human angiotensin-converting enzyme to said patient, thereby inhibiting the N-terminal site of human angiotensin-converting enzyme.

21. The method of claim 20, wherein said inhibiting further comprises regulating the proliferation of haematopoietic strain cells in a patient undergoing cancer treatment.

22. A method for inhibiting human angiotensin-converting enzyme comprising administering an effective amount of the peptide claim 13 to a subject in need thereof.

23. The method of claim 22 that comprises administering said peptide to a subject undergoing aggressive chemotherapy.

24. The method of claim 22 comprises administering said peptide to a subject undergoing radiotherapy.

25. A peptide derivative having the formula:

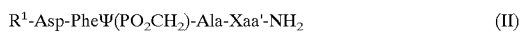
$$\text{Ac-Asp-}_{(R)}\text{Phe-}\Psi(PO_2CH_2)\text{-}_{(S)}\text{Ala-Ala-NH}_2 \quad (III)$$

wherein:

-Ac represents the acetyl group, and $\Psi(PO_2CH_2)$ indicates that the peptide bond (CONH) between Phe and Ala has been replaced by the phosphonic bond $(PO_2CH_2)$.

26. A pharmaceutical formulation comprising a peptide derivative according to claim 25.

27. A method for inhibiting the N-terminal site of human angiotensin-converting enzyme in a patient comprising
administering an amount of the peptide derivative of claim 25 effective to inhibit human angiotensin-converting enzyme to said patient, thereby inhibiting the N-terminal site of human angiotensin-converting enzyme.

28. The method of claim 27, wherein said inhibiting further comprises regulating the proliferation of haematopoietic strain cells in a patient undergoing cancer treatment.

29. A method for inhibiting human angiotensin-converting enzyme comprising administering an effective amount of the peptide of claim 22 to a subject in need thereof.

30. The method of claim 29 that comprises administering said peptide to a subject undergoing aggressive chemotherapy.

31. The method of claim 29, that comprises administering said peptide to a subject undergoing radiotherapy.

* * * * *